United States Patent [19]
Chang

[11] Patent Number: 5,139,014
[45] Date of Patent: Aug. 18, 1992

[54] MASSAGER WITH MAGNETIC PROTUBERANCES

[76] Inventor: Yih-Jong Chang, P.O. Box 82-144, Taipei, Taiwan

[21] Appl. No.: 706,383

[22] Filed: May 28, 1991

[51] Int. Cl.⁵ .................................... A61H 15/00
[52] U.S. Cl. ................................ 128/57; 128/60; 128/24.3
[58] Field of Search ............ 128/57, 64, 41, 60, 128/61, 58, 59, 62 R, 24.3; 74/558

[56] References Cited

U.S. PATENT DOCUMENTS

| | | | |
|---|---|---|---|
| 3,848,588 | 11/1974 | Miquel | 128/41 |
| 4,052,982 | 10/1977 | Ozeryansky | 128/57 |
| 4,744,350 | 5/1988 | Sato | 128/24.3 |

FOREIGN PATENT DOCUMENTS 1580112  7/1970  Fed. Rep. of Germany ........ 74/558

Primary Examiner—Robert A. Hafer
Assistant Examiner—David J. Kenealy
Attorney, Agent, or Firm—Alfred Lei

[57] ABSTRACT

This invention relates to a massager and in particular to a massage member having a semi-circular cross section and a plurality of solid and hollow round-headed protuberances on the surface, a plurality of magnets each fitted into one of the hollow round-headed protuberances of the massage member, a leather envelope formed with a plurality of holes adapted to receive the round-headed protuberances of the massage member, and two retainers each mounted at an end of the massage member.

2 Claims, 5 Drawing Sheets

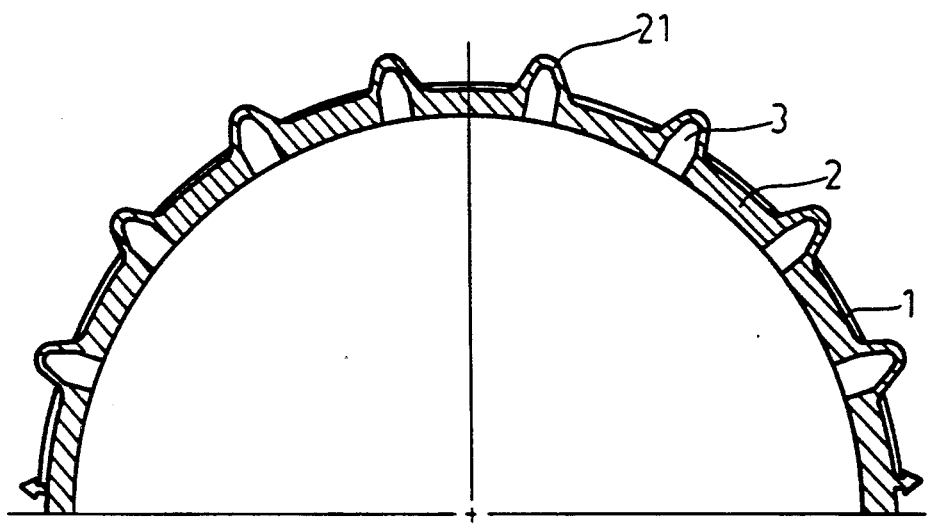
F I G. 2
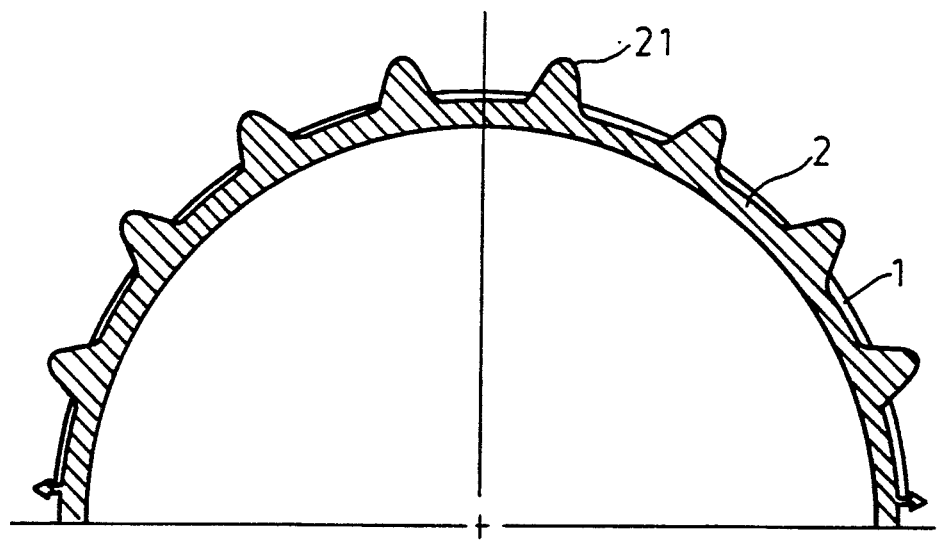
F I G. 3

MASSAGER WITH MAGNETIC PROTUBERANCES

BACKGROUND OF THE INVENTION

It is found that the prior art hand massager with round-headed protuberances on the market cannot provide sufficient stimulation and so it can only be used for finger massage, but not veins and vital points. Further, there is a ball massager which is provided with magnetic protuberances for massage and magnetic remedy on sale, but such massager is too heavy and inconvenience in use.

Therefore, it is an object of the present invention to provide a massager which may obviate and mitigate the above-mentioned drawbacks.

SUMMARY OF THE INVENTION

This invention relates to an improved massager.

It is the primary object of the present invention to provide a massager which may apply to a steering wheel so that the driver may massage his hand in driving.

It is another object of the present invention to provide a massager which may keep up the one's spirit.

It is still another object of the present invention to provide a massager which may make the user recover from fatigue.

It is still another object of the present invention to provide a massager which is simple in construction.

Other objects and merits and a fuller understanding of the present invention will be obtained by those having ordinary skill in the art when the following detailed description of the preferred embodiment is read in conjunction with the accompanying drawings.

BRIEF DESCRIPTION OF THE DRAWINGS

FIG. 2 is a sectional view of the hollow round-headed protuberance of the massager;

FIG. 3 is a sectional view of the solid round-headed protuberance of the massager;

DETAILED DESCRIPTION OF THE PREFERRED EMBODIMENT

Figure 1:
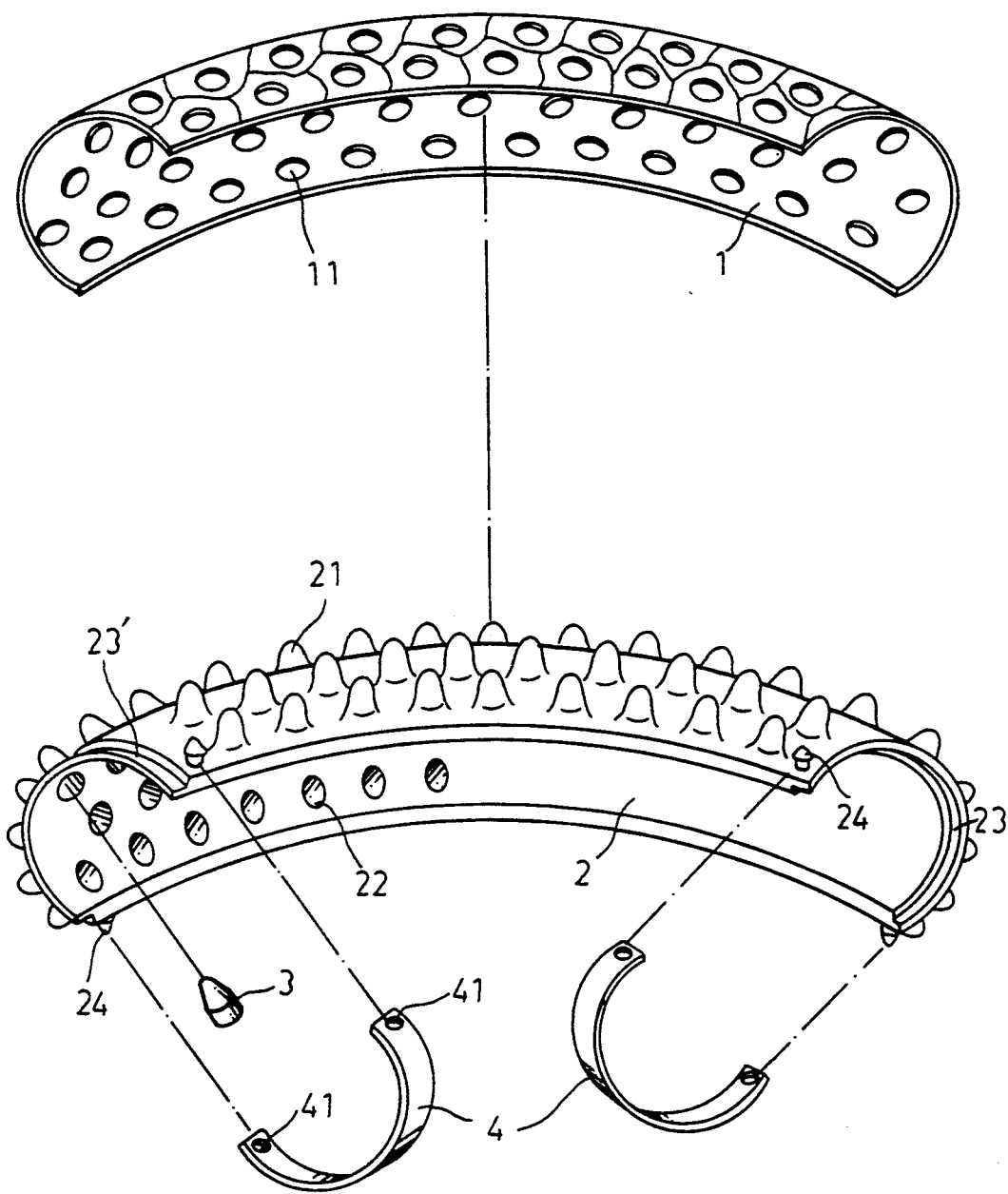
FIG. 1 is an exploded view of a massager according to the present invention.
Figure 4:
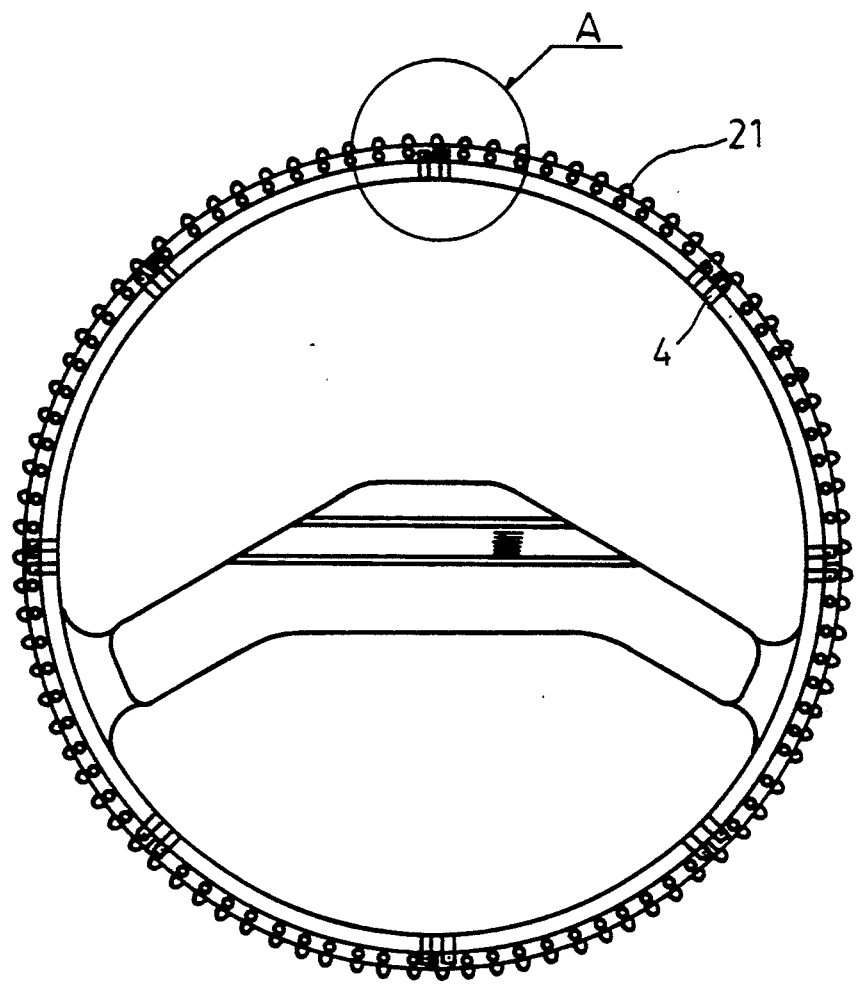
FIG. 4 shows the way to apply the present invention to a steering wheel.

With reference to the drawings and in particular to FIG. 1 thereof, the massager according to the present invention mainly comprises a leather envelope 1, a massage member 2, a plurality of magnets 3, and two retainers 4. The massage member 2 is preferably made of rubber or plastic with medium hardness. The massage member 2 has a semi-circular cross section and a plurality of round-headed protuberances 21 on the surface. Some of the round-headed proturberances 21 are solid and the other are hollow in structure. The solid round-headed protuberance 21 is designed for finger massage while the hollow round-headed protuberance 21 is formed with a recess 22 for receiving a magnet 3 and designed for finger massage as well as magnetic remedy. Further, the massage member 2 is provided at one end with a male connecting portion 23 and a female connecting portion 23' at the other so that a plurality of massage member 2 may be joined together. On both ends of the massage member 2 there is a projection 24. When a plurality of massage members 2 are mounted on a steering wheel (see FIG. 4) or a ring member (see FIG. 7), the holes 41 of the retainers 4 are engaged with the protuberances 24 of the massage member 2. The leather envelope 1 is formed with a plurality of holes 11 adapted to receive the round-headed protuberances 21 so as to absorb sweat and to keep the surface of the massage member 2 from being damaged.

As shown in FIGS. 2 and 3, the solid round-headed protuberance 21 is designed for finger massage while the hollow round-headed protuberance 21 is provided with a magnet in its recess 22 and designed for finger massage as well as magnetic remedy.

Figure 5:
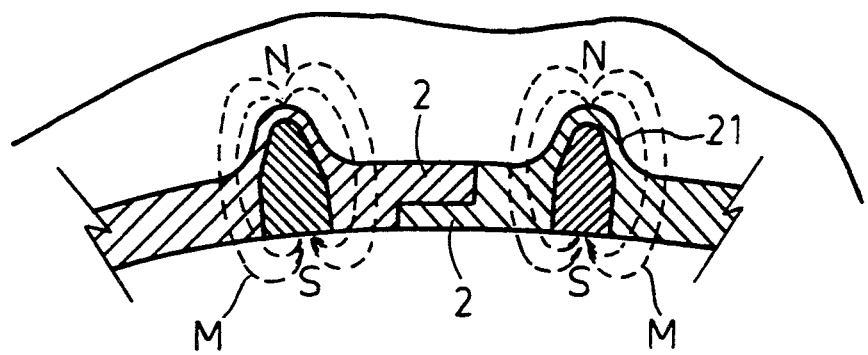
FIG. 5 shows the principle of the present invention.

FIG. 5 shows the principle of the present invention. As illustrated, the round-headed protuberance 21 will continuously emit magnet lines M from the North pole to the South pole so that when the body is in contact with the round-headed protuberance 21, the veins and vital points of the body will be appropriately stimulated hence achieving the purpose of massage. Further, the magnetic lines of force will promote the blood circulation as well as metabolism thereby keeping the health of the user.

Figure 7:
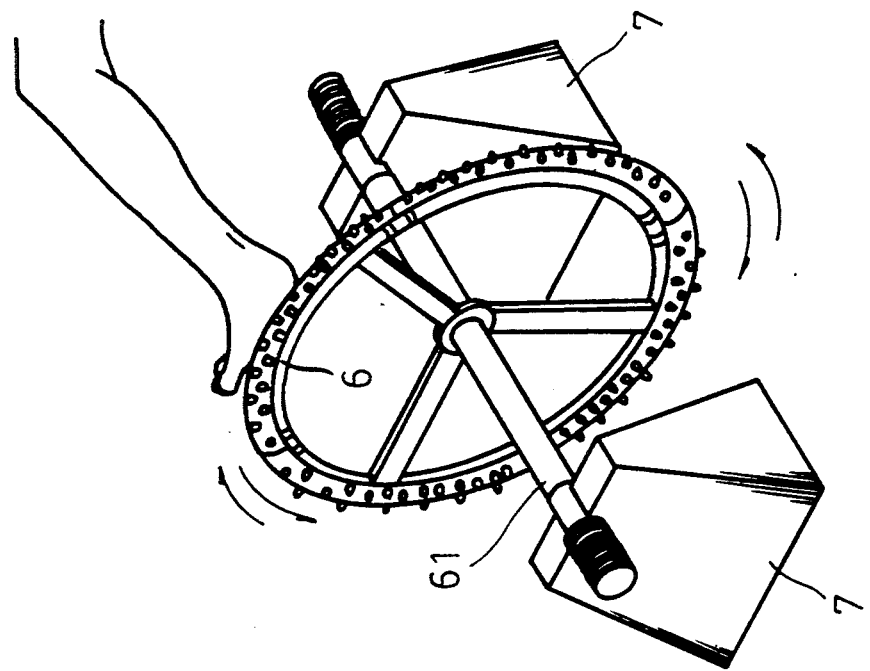
FIG. 7 shows a second embodiment of the present invention.
Figure 6:
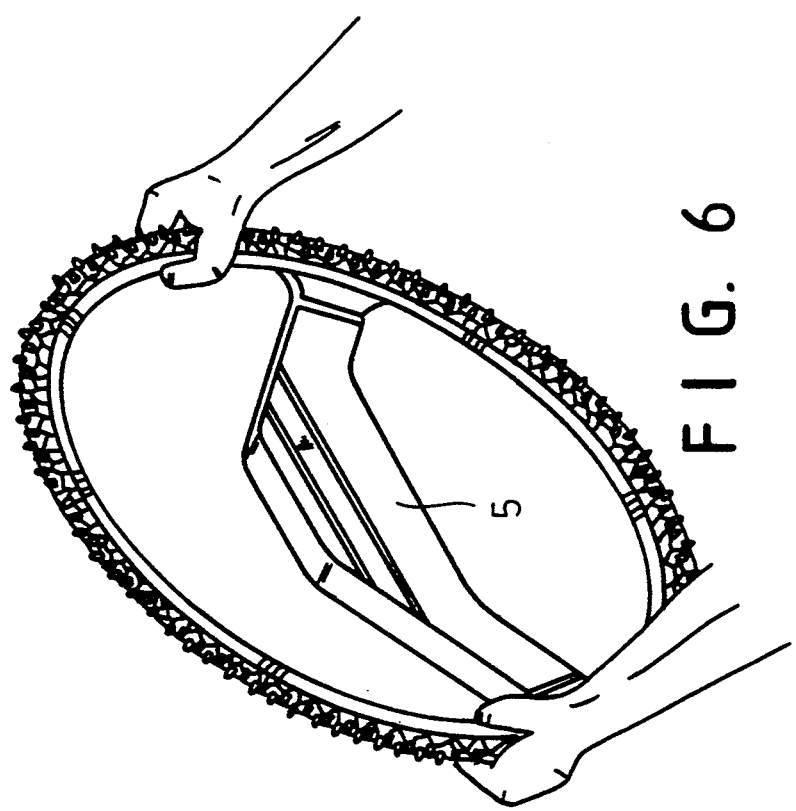
FIG. 6 shows a first embodiment of the present invention.
Figure 8:
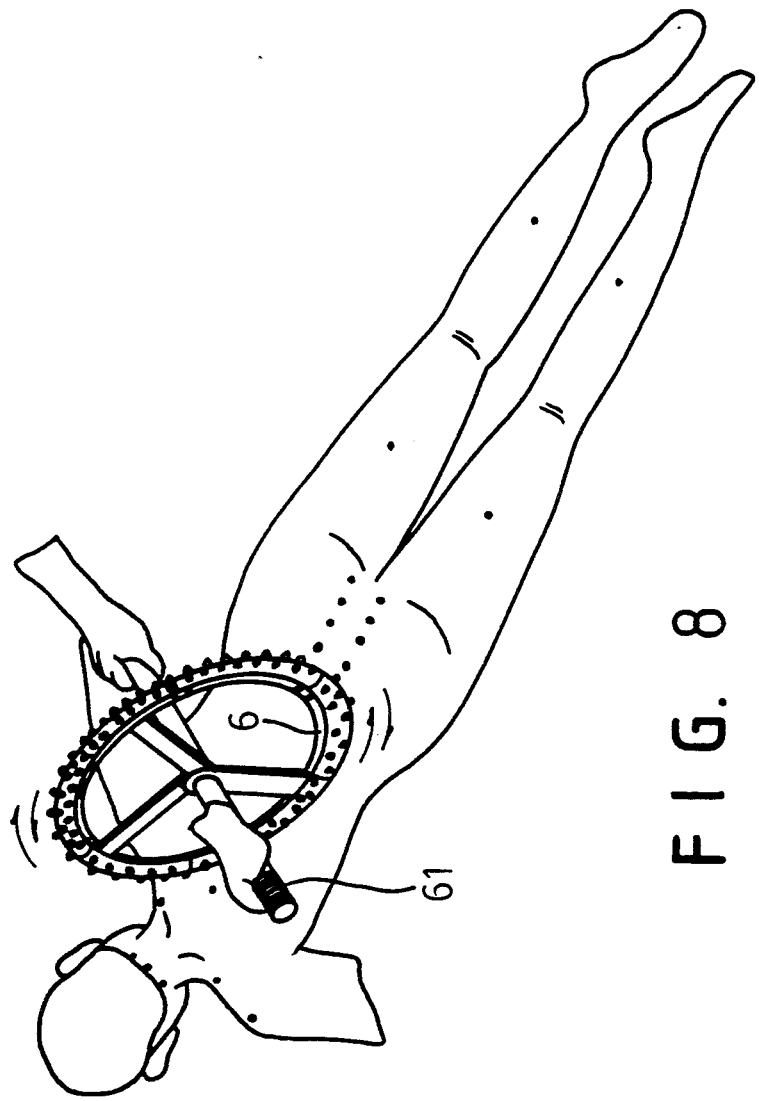
FIG. 8 shows a third embodiment of the present invention.

FIGS. 6 through 8 show different applications of the present invention. As may be seen, the massager may be used to massage the user's hands and prevent the hands from slipping when applied to a steering wheel. In addition, the massager may be applied to a ring member 6 with an axle 61 supported by a block 7 at both ends so that the massager may be rotated through an angle of 360 degrees thereby enabling the foot to be massaged conveniently. Besides, the massager may be used to massage the body as shown in FIG. 8.

Although the present invention is described with a certain degree of particularity, it is understood that the present disclosure is made by way of example only and that numerous changes in the detail of construction and the combination and arrangement of parts may be resorted to without departing from the spirit and scope of the invention as hereinafter claimed.

I claim:

1. A massager comprising:
    a massage member provided with a semi-circular cross section having a concave inner portion and convex outer portion, with a plurality of solid and hollow round-headed protuberances projecting from the convex outer portion;
    a plurality of magnets each fitted into one of the hollow round-headed protuberances of said massage member;
    a leather envelope formed with a plurality of holes adapted to receive the round-headed protuberances of said massage member; and
    two retainers each mounted at an end of said massage member.

2. The massager as claimed in claim 1, wherein each end of said massage member is provided with a projection for engaging with said retainer.

* * * * *